(12) United States Patent
Gilchrist et al.

(10) Patent No.: US 12,718,947 B2
(45) Date of Patent: Aug. 25, 2026

(54) SYSTEMS, METHODS, AND DEVICES FOR DETECTING VIRAL RESPIRATORY ILLNESS IN PRESYMPTOMATIC AND ASYMPTOMATIC INFECTED PERSONS

(71) Applicant: Research Triangle Institute, Research Triangle Park, NC (US)

(72) Inventors: Kristin Hedgepath Gilchrist, Rockville, MD (US); Meghan Sarah Hegarty-Craver, Durham, NC (US); Dorota Temple, Cary, NC (US); Robert Furberg, Chapel Hill, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 0 days.

(21) Appl. No.: 18/398,623

(22) Filed: Dec. 28, 2023

(65) Prior Publication Data

US 2024/0127954 A1 Apr. 18, 2024

Related U.S. Application Data

(63) Continuation of application No. PCT/US2022/073348, filed on Jul. 1, 2022.
(Continued)

(51) Int. Cl.
*G16H 50/20* (2018.01)
*A61B 5/00* (2006.01)
(Continued)

(52) U.S. Cl.
CPC ........... *G16H 50/20* (2018.01); *A61B 5/0022* (2013.01); *A61B 5/0024* (2013.01); *A61B 5/01* (2013.01);
(Continued)

(58) Field of Classification Search
None
See application file for complete search history.

(56) References Cited

U.S. PATENT DOCUMENTS 10,252,145 B2 4/2019 Tran et al.
10,264,971 B1 * 4/2019 Kennedy ............. A61B 5/6804
(Continued)

FOREIGN PATENT DOCUMENTS

WO 2010077997 A2 7/2010
WO 2016037091 A1 3/2016
(Continued)

OTHER PUBLICATIONS

ISA/KR, International Search Report and Written Opinion for corresponding PCT Patent Application No. PCT/US2022/073348, mailed Nov. 2, 2022, 9 pages.
(Continued)

*Primary Examiner* — John A Pauls
(74) *Attorney, Agent, or Firm* — NK Patent Law

(57) ABSTRACT

Disclosed herein are systems, methods, and devices of detecting illness in presymptomatic and asymptomatic infected persons using wearable sensor technology. In a first embodiment, a method is implemented on a computing device, the method includes receiving first sensor data associated with the person over a first period of time and applying the first sensor data to a multi-variate detection model. The method further includes receiving second sensor data associated with the person over a second period of time and applying the second sensor data to the multi-variate detection model. Further the method includes determining a probability value of the illness in the person using the multi-variate detection model and transmitting the probability value to a user interface (UI).

12 Claims, 7 Drawing Sheets

Related U.S. Application Data

(60) Provisional application No. 63/217,787, filed on Jul. 2, 2021.

(51) Int. Cl.

| | |
|---|---|
| ***A61B 5/01*** | (2006.01) |
| ***A61B 5/024*** | (2006.01) |
| ***A61B 5/11*** | (2006.01) |
| ***A61B 5/1455*** | (2006.01) |
| ***A61B 5/28*** | (2021.01) |
| ***A61B 5/352*** | (2021.01) |
| ***G16H 10/60*** | (2018.01) |

(52) U.S. Cl.

CPC ........ *A61B 5/02405* (2013.01); *A61B 5/1102* (2013.01); *A61B 5/1118* (2013.01); *A61B 5/1455* (2013.01); *A61B 5/28* (2021.01); *A61B 5/352* (2021.01); *A61B 5/4266* (2013.01); *A61B 5/681* (2013.01); *A61B 5/6823* (2013.01); *A61B 5/742* (2013.01); *G16H 10/60* (2018.01); *A61B 2505/07* (2013.01); *A61B 2560/045* (2013.01); *A61B 2560/0462* (2013.01); *A61B 2562/0219* (2013.01)

(56) References Cited

U.S. PATENT DOCUMENTS

| | | | | |
|---|---|---|---|---|
| 2005/0234313 | A1 * | 10/2005 | Rowlandson ............ | A61B 5/08<br>600/509 |
| 2006/0084848 | A1 * | 4/2006 | Mitchnick ............. | A61B 5/411<br>600/595 |
| 2010/0280564 | A1 | 11/2010 | Zhang | |
| 2011/0119212 | A1 * | 5/2011 | De Bruin ............... | A61B 5/369<br>706/12 |
| 2016/0292365 | A1 | 10/2016 | Chi | |
| 2017/0238858 | A1 * | 8/2017 | Yang .................. | A61B 5/02416 |
| 2017/0330438 | A1 * | 11/2017 | Howard ............. | A61B 5/02438 |
| 2018/0000428 | A1 | 1/2018 | Swiston et al. | |
| 2019/0150787 | A1 * | 5/2019 | Murray ................ | A61B 5/0816 |
| 2020/0060613 | A1 | 2/2020 | Lee | |
| 2021/0321942 | A1 * | 10/2021 | Pushpala .............. | A61B 5/0205 |
| 2022/0164602 | A1 * | 5/2022 | Frtunikj .............. | G06F 18/2115 |

FOREIGN PATENT DOCUMENTS

| | | | | |
|---|---|---|---|---|
| WO | WO-2018072035 A1 * | 4/2018 | ............. | G06F 17/15 |
| WO | WO-2021222601 A1 * | 11/2021 | ............. | G16H 15/00 |

OTHER PUBLICATIONS

IPEA/US, International Preliminary Report on Patentability for corresponding PCT Patent Application No. PCT/US2022/073348, dated Oct. 25, 2023, 8 pages.

Seshadri, D. R. et al.: “Wearable Sensors for COVID-19: A Call to Action to Harness Our Digital Infrastructure for Remote Patient Monitoring and Virtual Assessments”, Frontiers in Digital Health, www.frontiersin.org, Jun. 2020, vol. 2, Article 8, pp. 1-11.

Calderón-Gómez, H. et al.: “Telemonitoring System for Infectious Disease Prediction in Elderly People Based on a Novel Microservice Architecture”, IEEE Access, Jun. 29, 2020, vol. 8, pp. 118340-118354.

Ip.com: Technology Vitality Report “Analytical Methods for Detection of Illness Using Wearable . . . ”, Aug. 25, 2020, pp. 1-11.

* cited by examiner

SYSTEMS, METHODS, AND DEVICES FOR DETECTING VIRAL RESPIRATORY ILLNESS IN PRESYMPTOMATIC AND ASYMPTOMATIC INFECTED PERSONS

CROSS-REFERENCE TO RELATED APPLICATION

This application is a continuation application of PCT patent application no. PCT/US2022/073348 titled "SYSTEMS, METHODS, AND DEVICES FOR DETECTING VIRAL RESPIRATORY ILLNESS IN PRESYMPTOMATIC AND ASYMPTOMATIC INFECTED PERSONS," filed Jul. 1, 2022, which claims the benefit of priority of U.S. provisional patent application No. 63/217,787 titled "SYSTEMS, METHODS, AND DEVICES FOR DETECTING VIRAL RESPIRATORY ILLNESS IN PRESYMPTOMATIC AND ASYMPTOMATIC INFECTED PERSONS," filed Jul. 2, 2021, which are all incorporated herein by their entireties by this reference.

STATEMENT REGARDING FEDERALLY SPONSORED RESEARCH OR DEVELOPMENT

This invention was made with government support under HR0011-18-1-0035 awarded by the Defense Advanced Research Projects Agency, and HDTRA1-18-1-0007 awarded by the Defense Threat Reduction Agency. The government has certain rights in the invention.

TECHNICAL FIELD

The present disclosure relates generally to medical diagnostic methods and devices. More specifically; methods, systems, and devices are disclosed for detection of illness in presymptomatic and asymptomatic infected persons.

BACKGROUND

Coronavirus disease spread rapidly around the world during the year 2020. One of the primary reasons was presymptomatic and asymptomatic transmission of the disease. The main detection tools available were contract tracing and wide spread testing of individuals that may have come in contact with a possible infectious person. Several attempts were made to develop mobile applications for smartphones that would perform contact tracing automatically. Bluetooth® proximity information and/or global positioning system (GPS) location data was used to detect and to notify an individual if they were exposed to another individual who was later diagnosed with Coronavirus disease. However, mobile device users were hesitant to adopt the contact tracing for privacy concerns, and both individuals needed to have the mobile application installed and running. Additionally, the mobile applications could only acquire limited data about the contact time and distance, without much certainty that the infection had actually spread during the event.

Accordingly, there remains a need for improved systems, methods, and devices of detecting illness in presymptomatic and asymptomatic persons within a non-clinical setting. Additionally, such systems, methods, and devices could improve overall health and wellbeing by early warnings of when an individual should seek treatment.

SUMMARY OF THE DISCLOSURE

Disclosed herein are systems, methods, and devices of detecting illness in presymptomatic and asymptomatic infected persons using wearable sensor technology. In a first embodiment, a method is implemented on a computing device, the method includes receiving first sensor data associated with the person over a first period of time and applying the first sensor data to a multi-variate detection model. The method further includes receiving second sensor data associated with the person over a second period of time and applying the second sensor data to the multi-variate detection model. Further the method includes determining a probability value of the illness in the person using the multi-variate detection model and transmitting the probability value to a user interface (UI).

In some embodiments the first time period may be associated with a pre-illness time period and the second time period may be associated with a presymptomatic time period of the illness.

In some embodiments, the first time period may be associated with a pre-illness time period and the second time period may be associated with an asymptomatic time period of the illness.

In some embodiments, the first time period may be associated with a presymptomatic time period of the illness and the second time period may be associated with a post-illness time period.

In some embodiments, the first time period may be associated with an asymptomatic time period of the illness and the second time period may be associated with a post-illness time period.

In some embodiments, the first sensor data may be received from at least one sensor positioned on a wearable health device.

In some embodiments, the wearable health device may be at a smartwatch.

In some embodiments, the smartwatch may be at least one of a Garmin® smartwatch, an Apple Watch®, a Samsung Galaxy® Watch, a Fitbit® Sense, a Withings® ScanWatch, a Withings® Move ECG, an Amazfit® Smartwatch 2, or the like.

In some embodiments, the second sensor data may be received from the at least one sensor positioned on the wearable health device.

In some embodiments, the computing device may be embedded within the wearable health device.

In some embodiments, the computing device may be configured to wirelessly receive the first sensor data over a personal area network (PAN).

In some embodiments, the PAN may be compliant to a least one version of the Bluetooth® communication protocol.

In some embodiments, the computing device may be embedded within at least one of a smartphone and a tablet device.

In some embodiments, the computing device may be configured to wirelessly receive the first sensor data over a wireless local area network (WLAN).

In some embodiments, the WLAN may be compliant to at least one version of the 802.11 communication protocol.

In some embodiments, the computing device may be configured to wirelessly receive the first sensor data over a wide area network (WAN).

In some embodiments, the WAN may be at least one of a 3G network, a 4G network, a 5G network, or the like.

In some embodiments, the computing device may be at least one a server, a personal computer (PC), a laptop, or the like.

In some embodiments, the at least one sensor may be a chest positioned ECG sensor.

In some embodiments, the computing device may be implemented within a medical device.

In some embodiments, the illness may be an infectious disease.

In some embodiments, the infectious disease may be associated with an influenza virus. In other embodiments, the infectious disease may be associated with a novel virus.

In some embodiments, the novel virus may be a severe acute respiratory syndrome (SARS) coronavirus (SARS-CoV). In other embodiments, the novel virus may be a Middle East respiratory syndrome (MERS) coronavirus (MERS-CoV).

In some embodiments, the illness may be at least one of cardiovascular disease, diabetes, chronic respiratory disease, cancer, or the like.

In some embodiments, the first sensor data may be first electrocardiogram (ECG) data and the second sensor may be second ECG data.

In some embodiments, the first sensor data may be first ballistocardiogram (BCG) data and the second sensor data may be second BCG data.

In some embodiments, the first sensor data may be first photoplethysmography (PPG) data and the second sensor data may be second PPG data.

In some embodiments, the first sensor data may be first oxygen saturation data ($SpO_2$) data and the second sensor data may be second $SpO_2$ data.

In some embodiments, the first sensor data may be first body temperature data and the second sensor data may be second body temperature data.

In some embodiments, the first sensor data may be first respiration data and the second sensor data may be second respiration data.

In some embodiments, the first sensor data may be first perspiration data and the second sensor data may be second perspiration data.

In some embodiments, the first sensor data may include a first digital representation of a first analog wave form received from a sensor positioned on the person during the first time period and the second sensor data may include a second digital representation of a second analog wave form received from the sensor positioned on the person during the second time period.

In some embodiments, the method may further include applying a first time of day associated with the first time period to the multi-variate detection model and applying a second time of day associated with the second time period to the multi-variate detection model.

In some embodiments, the method may further include applying a first day of week associated with the first time period to the multi-variate detection model and applying a second day of week associated with the second time period to the multi-variate detection model.

In some embodiments, the method may further include applying first activity level data of the person associated with the first time period to the multi-variate detection model and applying second activity level data of the person associated with the second time period to the multi-variate detection model.

In some embodiments, the first activity level data may be based on first accelerometer data received from an accelerometer positioned on the person during the first time period and the second activity level data is based on second accelerometer data received from the accelerometer positioned on the person during the second time period.

In some embodiments, the method may further include applying first body position data of the person associated with the first time period to the multi-variate detection model and applying second body position data of the person associated with the second time period to the multi-variate detection model.

In some embodiments, the method may further include applying an age of the person to the multi-variate detection model.

In some embodiments, the method may further include applying a gender of the person to the multi-variate detection model.

In some embodiments, the method may further include applying a body mass index (BMI) of the person to the multi-variate detection model.

In some embodiments, first sensor data and the second sensor data each may include beat-to-beat (RR) interval data.

In some embodiments, the method may further include determining a magnitude, a slope, and a time period associated with at least one beat-to-beat (RR) interval within the first sensor data. The method may further include determining a magnitude, a slope, and a time period associated with at least one beat-to-beat (RR) interval within the second sensor data.

In some embodiments, the first sensor data and the second sensor data may each include heart rate variability (HRV) data.

In some embodiments, the person may be within a non-clinical setting when the first sensor data is obtained.

In some embodiments, the UI may be associated with the person.

In some embodiments, the UI may be embedded within at least one of a wearable health device, a smart watch, a smart phone, a tablet, a laptop, a PC, virtual assistant, and a smart television (TV).

In some embodiments, the multi-variate detection model includes at least one principal component analysis (PCA) method and/or at least one principal component analysis (PCA) method.

In some embodiments, the first sensor data and the second sensor data may each be collected at sampling rates greater than 10 Hertz.

In some embodiments, the first sensor data and the second sensor data may each be collected at sampling rates greater than 100 Hertz.

In some embodiments, the first sensor data and the second sensor data may each be collected at sampling rates greater than 200 Hertz.

In some embodiments, the method may further include applying a health history of the person to the multi-variate detection model In another embodiment, a computing device is disclosed for detecting illness in presymptomatic and asymptomatic infected persons using wearable sensor technology. The computing device includes a memory and at least one processor configured for performing a method. The method includes receiving first sensor data associated with the person over a first period of time and applying the first sensor data to a multi-variate detection model. The method further includes receiving second sensor data associated with the person over a second period of time and applying the second sensor data to the multi-variate detection model. Further the method includes determining a probability value of the illness in the person using the multi-variate detection model and transmitting the probability value to a UI.

In another embodiment, a non-transitory computer-readable storage medium is disclosed. The non-transitory computer-readable storage medium is configured for storing instructions to be implemented on a computing device including at least one processor. The instructions when executed by the at least one processor cause the at least one computing device to perform a method for detecting illness in presymptomatic and asymptomatic infected persons using wearable sensor technology. The method includes receiving first sensor data associated with the person over a first period of time and applying the first sensor data to a multi-variate detection model. The method further includes receiving second sensor data associated with the person over a second period of time and applying the second sensor data to the multi-variate detection model. Further the method includes determining a probability value of the illness in the person using the multi-variate detection model and transmitting the probability value to a UI.

The features and advantages described in this summary and the following detailed description are not all-inclusive. Many additional features and advantages will be apparent to one of ordinary skill in the art in view of the drawings, specification, and claims presented herein.

BRIEF DESCRIPTION OF THE DRAWINGS

The present embodiments are illustrated by way of example and are not intended to be limited by the figures of the accompanying drawings. In the drawings.

DETAILED DESCRIPTION

Figure 1:
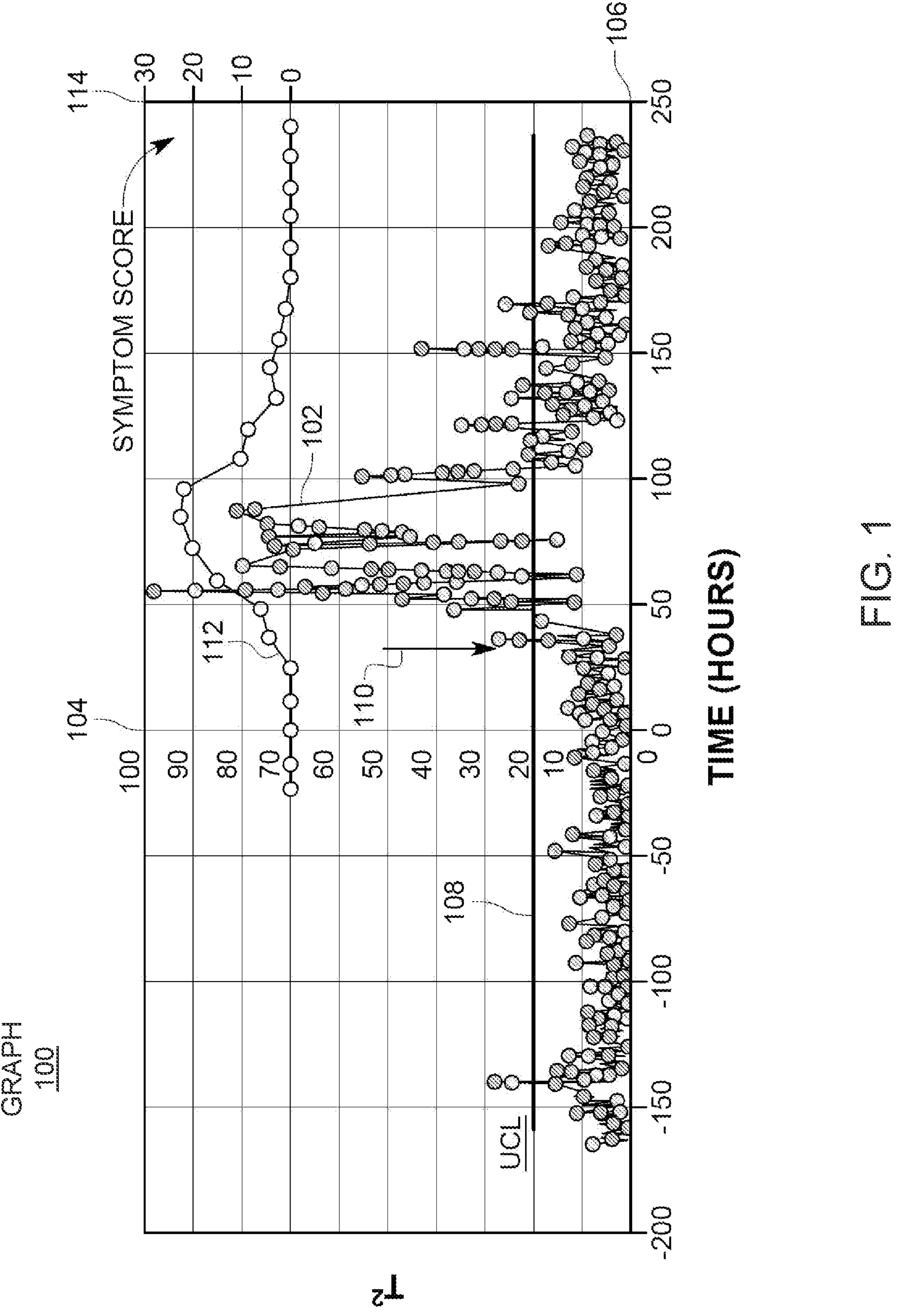
FIG. 1 depicts a graph illustrating a plot of Hoteling's T-squared distribution ($T^2$) statistics as a function of time for a subject infected with influenza in accordance with embodiments of the present disclosure.

The following description and drawings are illustrative and are not to be construed as limiting. Numerous specific details are described to provide a thorough understanding of the disclosure. However, in certain instances, well-known or conventional details are not described in order to avoid obscuring the description. References to "one embodiment" or "an embodiment" in the present disclosure can be, but not necessarily are, references to the same embodiment and such references mean at least one of the embodiments.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and is not intended to further limit the scope and meaning of the disclosure or of any exemplified term. Likewise, the disclosure is not limited to various embodiments given in this specification.

Without intent to limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

Disclosed herein are systems, methods, and devices of detecting illness in presymptomatic and asymptomatic infected persons using wearable sensor technology. A multi-variate detection model with feature standardization has been developed based on activity of monitored individuals. By performing 24 hour daily monitoring, relevant biomarkers for illness detection may be obtained.

Specifically, acquisition of raw data from wearable sensors is used to extract specific cardiac biomarkers that distinguish early warning markers of illness. A fitness monitor device may be used to provide the wearable sensors allowing easier acceptance by the individual to be monitored. The wearable sensors provide for collection of high-resolution and high-sampling rate data from wearable devices to enable high-resolution feature extraction from cardiac and other physiological signals. Additionally, evaluation of frequency-domain cardiac metrics adds for more specificity of detection of illness.

These techniques may also be used to detect significant physiological changes across a range of applications. Examples include changes in breathing or cardiac activity in response to air pollution, physiological indicators of impairment, or changes in autonomic function due to mild traumatic brain injury.

The multi-variate detection model includes analysis of cardiac and activity data from electrocardiogram sensors. These methods can be applied to any physiological sensor data including elelctrocardiogram (ECG) data, ballistocardiogram (BCG) data, oxygen saturation ($SpO_2$) data, photoplethysmography (PPG) data, body temperature data, body respiration data, body perspiration data, and/or the like.

For the algorithm to be accurate for illness detection, the large variability in baseline physiology across people, and the large number of confounding factors that influence physiological parameters within an individual have to be overcome. The multi-variate detection model uses a technique for standardizing sensor metrics that addresses both of these challenges.

First, a range of features are extracted from the raw sensor data in a defined time epoch (e.g., a five minute window). Metrics taken from ECG sensors and/or PPG sensors may include heart rate, time-domain heart rate variability (HRV) data (e.g. standard deviation of RR intervals), frequency domain HRV data (e.g. respiratory sinus arrhythmia or low frequency variability), and/or more advanced HRV data.

Second, these features are standardized within a subject based on a current state. The current state can be characterized by one or more parameters including time of day, activity level, body position, sleep state, heart rate, or heart rate variability. Comparable states in a window of previous data can be identified by setting thresholds around the current values for any of these state parameters. For example, a comparable time of day may be considered to be the current time plus or minus one hour.

Data from all states meeting the matching criteria form a population that can be used to compute a Z-score for any sensor metric. In multi-variate detection model the Z-score-metric(t) equals (metric(t) minus mean(metric in matching population)) divided by a standard deviation(metric in matching population. This standardization process is compatible with algorithms deployed for real time operation. A buffer of previous metric values can be stored for a designated period of time (e.g., one week) and continuously updated. The z-score values can be continuously computed using the values in the buffer. These standardized metrics can be used as inputs to the multi-variate detection model.

The multi-variate detection model uses anomaly detection. Healthy baseline data is characterized and an alert is generated for a statistically significant anomaly from this baseline. The multi-variate detection model with anomaly detection is based on principal component analysis (PCA) and multivariate process control (MVPC) techniques.

For each subject separately, a PCA is used to build a principal component model from the pre-exposure set of extracted features. The principal component model reduces the dimensionality of the data by projecting the measurements into a low-dimensional subspace that is defined by a small number of principal components. Next, the model applies post-exposure data for the subject to monitor the feature vector over time and detect any unusual variation in its values. For each data point, the algorithm computes Hoteling's T-squared distribution (T 2) and squared prediction error (SPE) statistics based on the principal components. When at least one of the statistics exceeds the control limit continuously for a selected period of time, the model issues an alert.

FIG. 1 depicts a graph 100 illustrating a plot 102 of $T^2$ statistics as a function of time for a subject infected with influenza in accordance with embodiments of the present disclosure. An axis 104 references values for the $T^2$ statistics and an axis 106 references time for the $T^2$ statistics. The time is measured with respect to the time of the inoculation (i.e. t=0). The subject tested positive for the influenza virus and exhibited significant symptoms that peaked approximately four days (100 hours) following the inoculation. A marker 108 is an upper control limit (UCL) calculated on the basis of pre-exposure data for the subject and assumes a significance level a of 0.001 which corresponds to the allowed range of values of approximately ±3.3 standard deviations a from the mean. A marker 110 indicates the time when a $T^2$ statistic exceeds the UCL continuously for at least 40 minutes. A plot 112 provides a total symptom score as a function of time for the subject. An axis 114 references values for the total symptom score.

Figure 2:
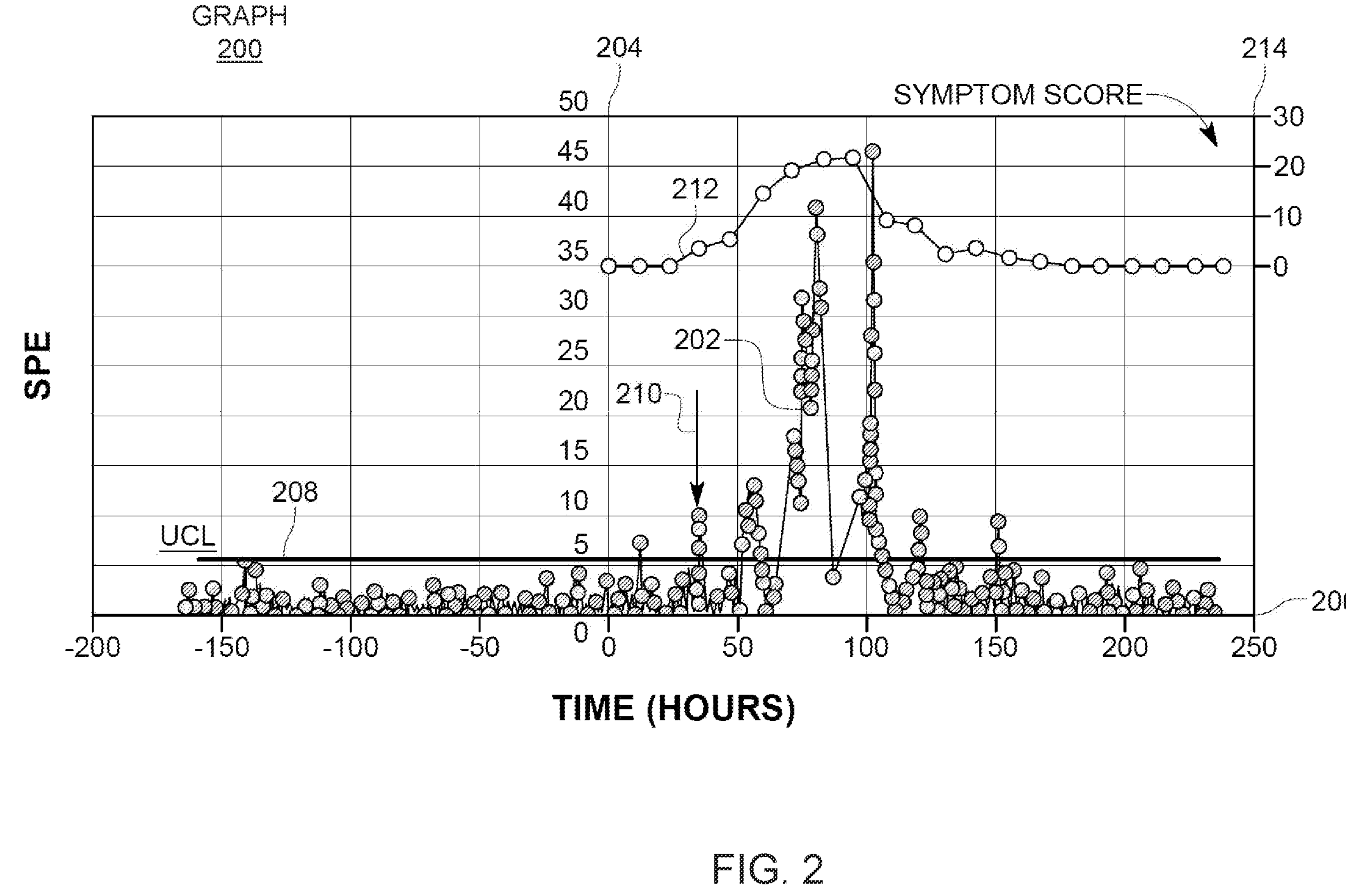
FIG. 2 depicts a graph illustrating a plot of squared prediction error (SPE) statistics as a function of time for the subject of FIG. 1 in accordance with embodiments of the present disclosure.

FIG. 2 depicts a graph 200 illustrating a plot 202 of SPE statistics as a function of time for the subject infected with influenza of FIG. 1 in accordance with embodiments of the present disclosure. An axis 204 references values for the SPE statistics and an axis 206 references time for the SPE statistics. As with FIG. 1, the time is measured with respect to the time of the inoculation (i.e. t=0). Also as with FIG. 1, a marker 208 is a UCL calculated on the basis of pre-exposure data for the subject and assumes a significance level a of 0.001 which corresponds to the allowed range of values of approximately ±3.3 standard deviations is from the mean. A marker 210 indicates the time when an SPE statistic exceeds the UCL continuously for at least 40 minutes. A plot 212 provides a total symptom score as a function of time for the subject. An axis 214 references values for the total symptom score.

As depicted, the first unusual variation is detected at approximately t=35 hours and well before the timing of significant symptoms. For example, significant symptoms would mean symptoms of the type that would motivate the subject to seek medical attention in normal circumstances. This disclosed approach has also demonstrated success in detecting significant anomalies in asymptomatic subjects who tested positive for influenza infection.

The disclosed method is amenable to implementation in a near real-time illness detection system. Using the previously described buffer of past data, the PCA model and statistics can be computed at a specified interval (e.g., every hour) on the historical data excluding the most recent data. The statistics on that same PCA model can be computed on the most recent data to determine whether the recent data indicates a significant deviation from the historical buffer. The historical buffer can be continuously updated to remove long term trends not associated with illness (e.g., increased fitness level, weight loss, and/or the like).

For cardiac (ECG) data collection, approximately 250 Hertz sample rates enable extraction of inter-beat interval in the cardiac signals. Such high sample rates are essential for illness detection. Wearable watches that use PPG may be used for this purpose. Wearable watches can also enable raw data collection similar in resolution to feature extraction from a wearable ECG sensor. These wearable watches also extend to monitoring activity levels (e.g., accelerometers) and to monitoring body temperature. Activity levels and body temperature may also be collected at high sample rates (e.g. greater than 10 Hertz) for high resolution. Typical monitoring at lower rates (e.g. 1.0 Hertz) is insufficient for feature extraction needed to detect illness with high sensitivity and specificity.

Figure 3:
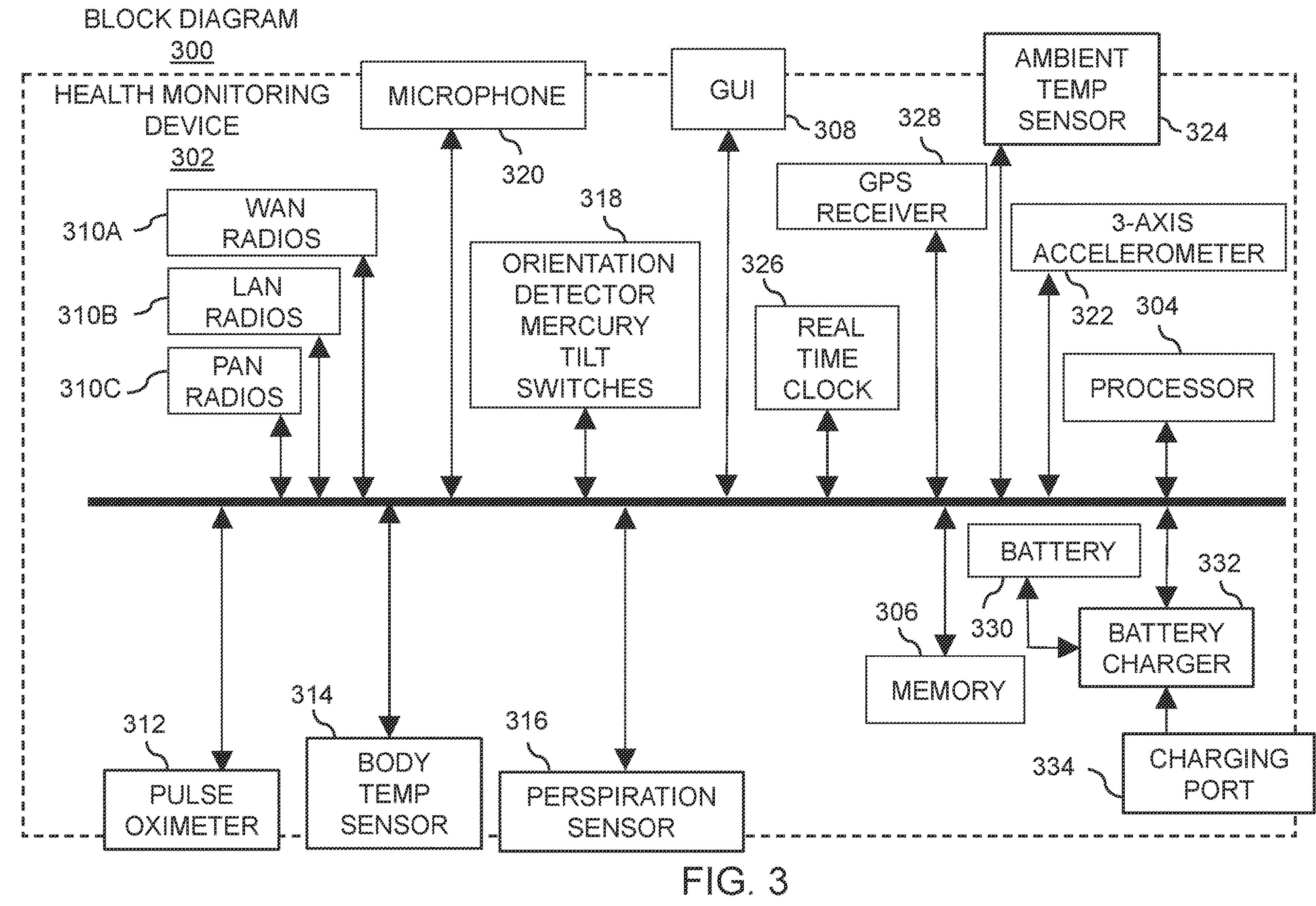
FIG. 3 depicts a block diagram illustrating a health monitoring device suitable for determining influenza infection in accordance with embodiments of the present disclosure.

FIG. 3 depicts a block diagram 300 illustrating a health monitoring device 302 in accordance with embodiments of the present disclosure. The health monitoring device 302 is suitable for collecting sensor data for use in the multi-variate detection model disclosed herein. The health monitoring device 302 includes a processor 304 and a memory 306. In some embodiments, the memory 306 or a portion of the memory 306 may be integrated with the processor 304. The memory 306 may include a combination of volatile memory and non-volatile memory. In some embodiments the processor 304 and the memory 306 may be embedded in a microcontroller. The processor 304 may be the Snapdragon® 4100 processor, the NXP Kinetix® microcontroller unit (MCU), or the like. The memory 306 may be configured for program instructions to implement the multi-variate detection model and/or send raw sensor data to a remote computing device. Also (not shown in FIG. 3), a plurality of analog-to-digital converters (ADCs) and digital-to-analog converters (DACs) may be used to interface the various components/sensors to the processor 304.

The health monitoring device 302 also includes a graphical user interface (GUI) 308. The GUI 308 may be a touchpad display. The health monitoring device 302 also includes wide area network (WAN) radios 310A, local area network (LAN) radios 310B, and personal area network (PAN) radios 310C. The WAN radios 310A may include 2G, 3G, 4G, and/or 5G technologies. The LAN radios 310B may include Wi-Fi technologies such as 802.11a, 802.11b/g/n, 802.11ac, 802.11.ax or the like circuitry. The PAN radios 310C may include Bluetooth® technologies.

The health monitoring device 302 also includes a pulse oximeter 312, a body temperature sensor 314, and a perspiration sensor 316 for obtaining the raw sensor data relating to multiple vital signs of the individual. The health monitoring device 302 also includes an orientation detector 318 including mercury tilt switches, a microphone 320, a three-axis accelerometer 322, and an ambient temperature sensor 324. The orientation detector 318 is configured to detect a relative position to gravity of the health monitoring device 302. The three axis accelerometer 322 is configured to detect instantaneous movements on x, y, and z-axis of the health monitoring device 302. The microphone 320 may be used to detect background noise that may be indicative of an ongoing activity of the individual. The ambient temperature sensor 324 may be used to better correlate the individual's body temperature from the body temperature sensor 314.

The health monitoring device 302 also includes a real time clock 326 for time stamping the raw sensor data and a global positioning system (GPS) 328 receiver determining a location. The health monitoring device 302 also includes a battery 330, a battery charger 332, and a charging port 324. The charging port 334 may be a wireless charging port.

Figure 4:
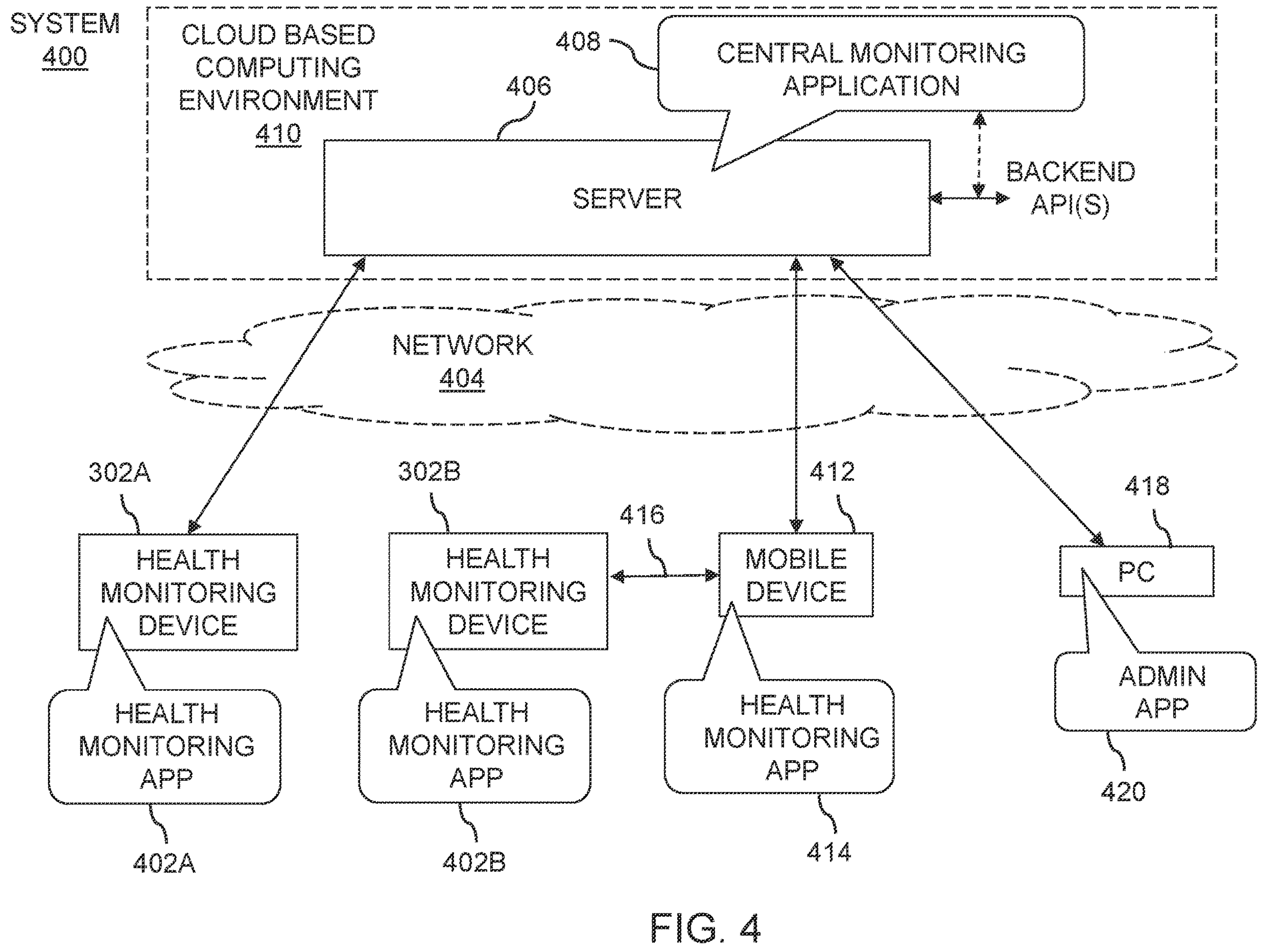
FIG. 4 depicts a diagram illustrating a system including the health monitoring device of FIG. 3, a mobile device, a server, and a personal computer (PC) in accordance with embodiments of the present disclosure.

FIG. 4 depicts a diagram illustrating a system 400 for monitoring for influenza infections in a plurality of subjects in accordance with embodiments of the present disclosure. The system 400 includes a first health monitoring device 302A monitoring a first subject for an influenza infection. A first health monitoring app 402A executes on the first health monitoring device 302A. The system 400 also includes a second health monitoring device 302B monitoring a second subject for an influenza infection. A second health monitoring app 402B executes on the second health monitoring device 302B.

The first health monitoring device 302A is configured (via the health monitoring app 402A) to communicate alerts and/or raw statistical data over a network 404 to a server 406. The network 404 may be any type or combination of wired, wireless, and/or optical networks. The network 404 may include the Internet. A central monitoring application 408 executes on the server 406. The server 406 is resident in a cloud based computing environment 410. In other embodiments, the server 406 may be housed a clinical trial facility, and/or other datacenter. Additionally, the central monitoring application 408 may communicate using one or more back-end application programming interfaces (APIs) to one or more other systems associated with collecting and analyzing the raw statistical data and/or the alerts. The backend APIs may communicate within the cloud based computing environment 410 and/or over the network 404.

The system 400 also includes a mobile device 412 executing a health monitoring app 414. The mobile device 412 may be a smart phone, a tablet, or the like. The mobile device 412 is configured to communication with the server 406 over the network 404. The mobile device 412 is also configured to communicate with the health monitoring device 302B over a PAN connection 116. The PAN connection 116 may be a Bluetooth® connection. In further embodiments, the PAN connection 116 may be a Bluetooth Low Energy (BLE) connection. The health monitoring app 414 is configured to collect alerts and/or raw statistical data over the PAN connection 116. The health monitoring app 414 may further process the raw statistical data and/or notify the user of alerts. The health monitoring app 414 may then send the raw statistical data, the alerts, and/or the additional processed data to the central monitoring application 408 via the network 404.

The server 406 also communicates with a personal computer (PC) 418 over the network 404. The PC 418 also executes an admin app 420 for providing administrative functions for the system 400. The admin app 420 may be provided via a web browser or an application specific program. In some embodiments, the PC 418 may be a laptop or a workstation. In other embodiments, the PC 418 may be a smart TV configured to operate a smart TV app.

Figure 5:
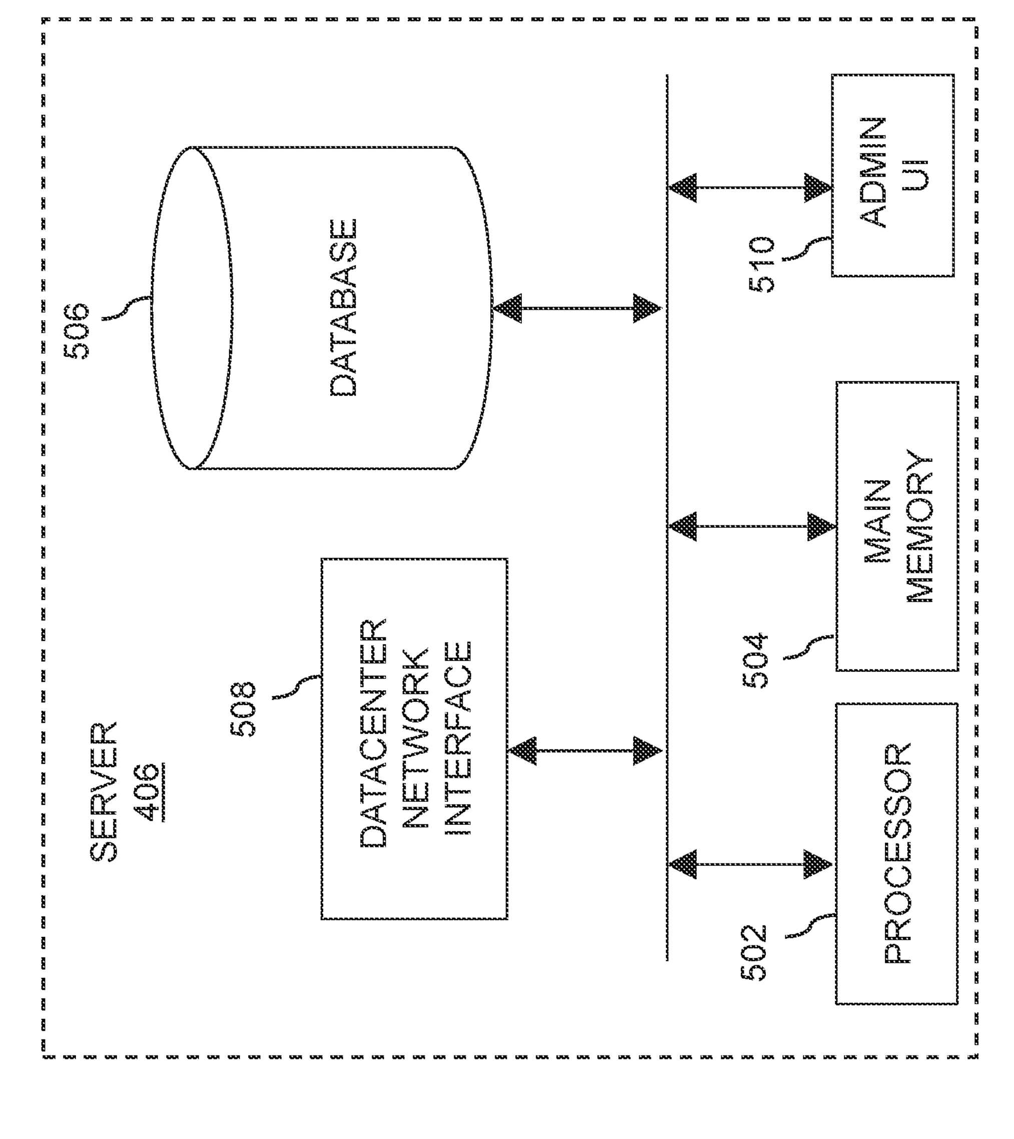
FIG. 5 depicts a block diagram illustrating the server of FIG. 4 in accordance with embodiments of the present disclosure.

FIG. 5 depicts a block diagram 500 illustrating the server 406 of FIG. 4 in accordance with embodiments of the present disclosure. The server 406 includes at least one processor 502, a main memory 504, a storage memory (e.g. database) 506, a datacenter network interface 508, and an administration user interface (UI) 510. The server 406 may be configured to host an Ubuntu® server or the like. In some embodiments the Ubuntu® server may be distributed over a plurality of hardware servers using hypervisor technology.

The processor 502 may be a multi-core server class processor suitable for hardware virtualization. The processor may support at least a 64-bit architecture and a single instruction multiple data (SIMD) instruction set. The main memory 504 may include a combination of volatile memory (e.g. random access memory) and non-volatile memory (e.g. flash memory). The database 506 may include one or more hard drives.

The datacenter network interface 508 may provide one or more high-speed communication ports to data center switches, routers, and/or network storage appliances. The datacenter network interface 508 may include high-speed optical Ethernet, InfiniBand (IB), Internet Small Computer System Interface (iSCSI), and/or Fibre Channel interfaces. The administration UI may support local and/or remote configuration of the server 406 by a datacenter administrator.

Figure 6:
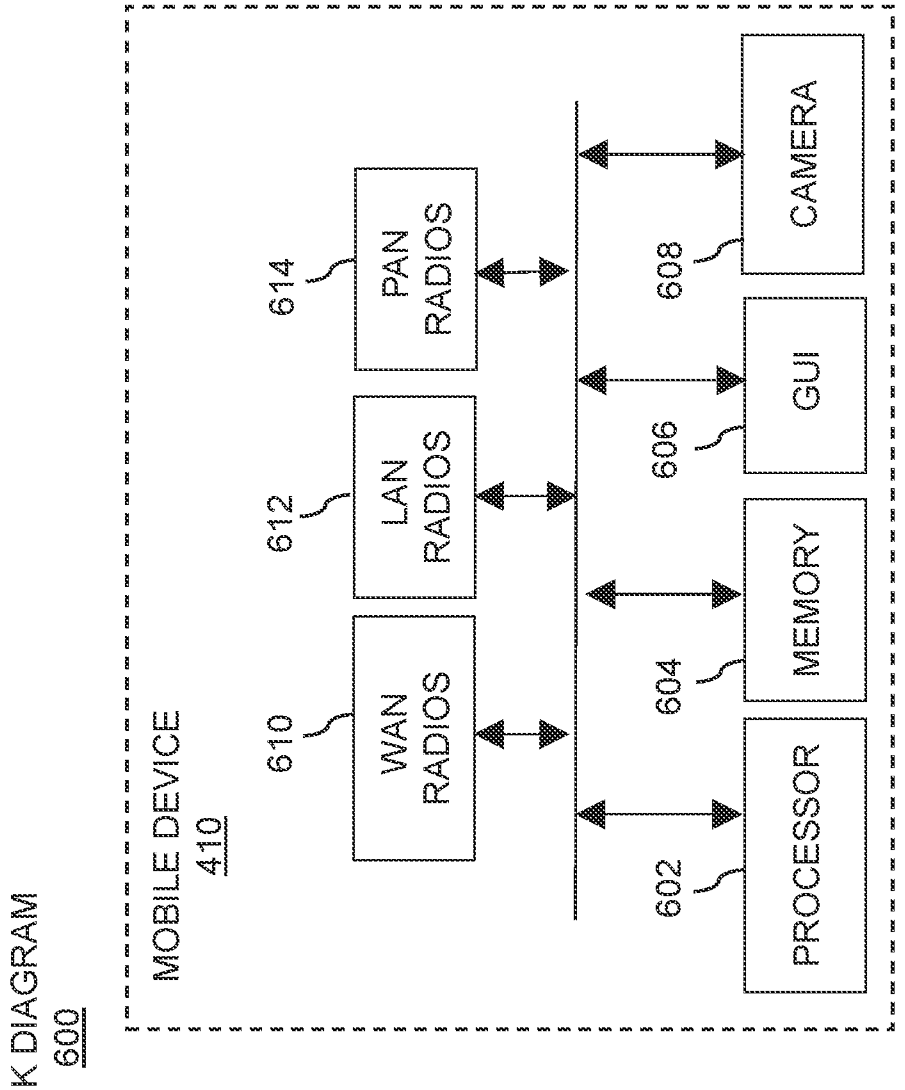
FIG. 6 depicts a block diagram illustrating the mobile device of FIG. 4 in accordance with embodiments of the present disclosure.

FIG. 6 depicts a block diagram 600 illustrating the mobile device 410 of FIG. 4 in accordance with embodiments of the present disclosure. The mobile device 410 may include at least a processor 602, a memory 604, a GUI 606, a camera 608, WAN radios 610, LAN radios 612, and personal area network (PAN) radios 614. In some embodiments, the mobile device 410 may be an iPhone® or an iPad®, using iOS® as an operating system (OS). In other embodiments, the mobile device 410 may be an Android® OS device.

In some embodiments, the processor 602 may be a mobile processor such as the Qualcomm® Snapdragon™ mobile processor. The memory 604 may include a combination of volatile memory (e.g. random access memory) and non-volatile memory (e.g. flash memory). The memory 604 may be partially integrated with the processor 602. The GUI 606 may be a touchpad display. The WAN radios 610 may include 2G, 3G, 4G, and/or 5G technologies. The LAN radios 612 may include Wi-Fi technologies such as 802.11a, 802.11b/g/n, 802.11ac, and/or 802.11ax circuitry. The PAN radios 614 may include Bluetooth® technologies. One or more of the PAN radios 614 may be configured to communicate with one or more of the PAN radios 310C of the health monitoring device 302.

Figure 7:
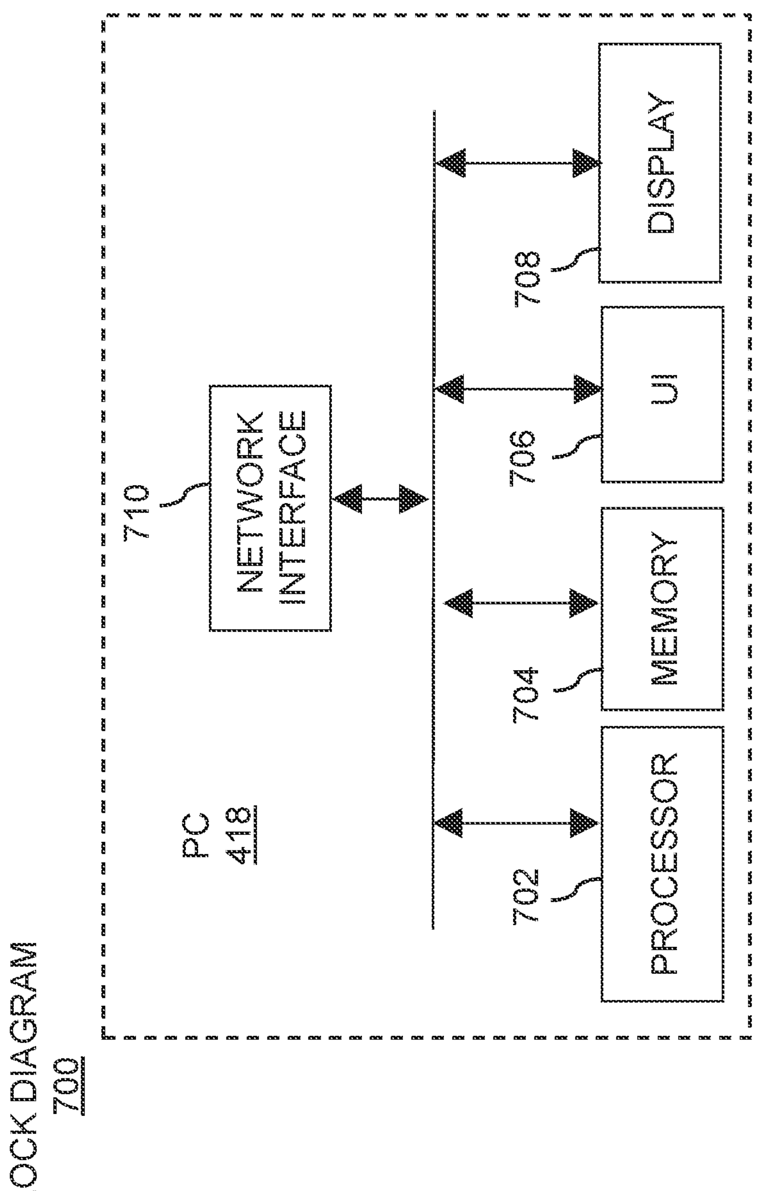
FIG. 7 depicts a block diagram illustrating the PC of FIG. 4 in accordance with embodiments of the present disclosure.

FIG. 7 depicts a block diagram 700 illustrating the PC 414 of FIG. 4 in accordance with embodiments of the present disclosure. The PC 414 may include at least one processor 702, at least one memory 704, a user interface (UI) 706, at least one display 708, and a network interface 710. In certain embodiments, the PC 414 may be a workstation class computing device. The processor 702 may be an Intel core i9-10900K desktop processor or the like. The memory 704 may include a combination of volatile memory (e.g. random access memory) and non-volatile memory (e.g. flash memory). The memory 704 may be partially integrated with the processor 702. The UI 710 may include a keyboard. The UI 710 may also include a mouse, at touchpad, or the like. In certain embodiments, the UI 710 may be integrated with the display 706. The display 708 may be a separate display or may be integrated with the other components (e.g., a laptop). The PC 414 may include an operating system (OS). The operating system (OS) may be a Windows® OS, a Macintosh® OS, a Linux® OS, or the like. The network interface 710 may be a wired Ethernet interface or a Wi-Fi interface. The PC 414 may be configured to access remote memory (e.g., network storage and/or cloud storage) via the network interface 710.

Numerous modifications and variations of the present disclosure are possible in view of the above teachings. It is understood that within the scope of the appended claims, the disclosure may be practiced otherwise than as specifically described herein.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including object oriented and/or procedural programming languages. For example, programming languages may include, but are not limited to: Ruby, JavaScript, Java, Python, Ruby, PHP, C, C++, C#, Objective-C, Go, Scala, Swift, Kotlin, OCaml, or the like.

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method implemented on a smart watch for detecting an infectious disease within a person during a non-symptomatic time period of the infectious disease in a non-clinical setting, the method comprising:
- applying an age, a gender, and a body mass index (BMI) of the person to a multi-variate detection model, wherein the multi-variate detection model includes a principal component analysis (PCA) model and a buffer for storing past data;
- collecting first cardiac data by sampling a photoplethysmography (PPG) sensor on the smart watch at a rate greater than 200 Hertz over a first time period and storing the first cardiac data in a buffer;
- collecting first activity level data by sampling an accelerometer on the smart watch at a rate greater than 10 Hertz over the first time period and storing the first activity level data in the buffer;
- applying the first cardiac data and the first activity level data to the multi-variate detection model;
- applying a first time of day associated with the first time period to the multi-variate detection model;
- applying first body position data of the person associated with the first time period to the multi-variate detection model;
- collecting second cardiac data by sampling the PPG sensor at a rate greater than 200 Hertz over a second time period and storing the second cardiac data in the buffer;
- collecting second activity level data by sampling the accelerometer at a rate greater than 10 Hertz over the second time period and storing the second activity level data in the buffer;
- applying a second time of day associated with the second time period to the multi-variate detection model;
- applying second body position data of the person associated with the second time period to the multi-variate detection model;
- characterizing the first cardiac data and the first activity level data as baseline data including:
  - associating the first time period with a non-infected time period of the person; and
  - determining an upper control limit based on the non-infected time period of the person;
- continuously updating the buffer to remove long term trends via the PCA model;
- determining in near real-time a statistically significant anomaly within the second cardiac data using the multi-variate detection model including the upper control limit, wherein the statistically significant anomaly is associated with the non-symptomatic time period of the infectious disease;
- upon determining the statistically significant anomaly, generating an alert indicative of the non-symptomatic time period of the infectious disease; and
- providing the alert during the non-symptomatic time period to a user interface (UI) on the smart watch, wherein the method is a non-invasive method implemented by the smart watch.

2. The method of claim 1, wherein the non-symptomatic time period is associated with a presymptomatic time period of the infectious disease.

3. The method of claim 1, wherein non-symptomatic time period is associated with an asymptomatic time period of the infectious disease.

4. The method of claim 1, wherein the first cardiac data and the second cardiac data each include beat-to-beat (RR) interval data.

5. The method of claim 1, wherein the first cardiac data and the second cardiac data each include heart rate variability (HRV) data.

6. The method of claim 1, wherein the multi-variate detection model further includes at least one multivariate process control (MVPC) method.

7. The method of claim 1 further comprising applying a health history of the person to the multi-variate detection model.

8. The method of claim 1, wherein the long term trends include at least one of increased fitness level and weight loss.

9. A smart watch for detecting an infectious disease within a person during a non-symptomatic time period of the infectious disease in a non-clinical setting, the smart watch comprising:
- a photoplethysmography (PPG) sensor;
- an accelerometer;
- a user interface (UI)
- a memory; and
- at least one processor configured for:
  - applying an age, a gender, and a body mass index (BMI) of the person to a multi-variate detection model, wherein the multi-variate detection model includes a principal component analysis (PCA) model and a buffer for storing past data;
  - collecting first cardiac data by sampling the PPG sensor at a rate greater than 200 Hertz over a first time period and storing the first cardiac data in a buffer;
  - collecting first activity level data by sampling the accelerometer at a rate greater than 10 Hertz over the first time period and storing the first activity level data in the buffer;

applying the first cardiac data and the first activity level data to the multi-variate detection model;

applying a first time of day associated with the first time period to the multi-variate detection model;

applying first body position data of the person associated with the first time period to the multi-variate detection model;

collecting second cardiac data by sampling the PPG sensor at a rate greater than 200 Hertz over a second time period and storing the second cardiac data in the buffer;

collecting second activity level data by sampling the accelerometer at a rate greater than 10 Hertz over the second time period and storing the second activity level data in the buffer;

applying a second time of day associated with the second time period to the multi-variate detection model;

applying second body position data of the person associated with the second time period to the multi-variate detection model;

characterizing the first cardiac data and the first activity level data as baseline data including:

associating the first time period with a non-infected time period of the person; and determining an upper control limit based on the non-infected time period of the person;

continuously updating the buffer to remove long term trends via the PCA model;

determining in near real-time a statistically significant anomaly within the second cardiac data using the multi-variate detection model including the upper control limit, wherein the statistically significant anomaly is associated with the non-symptomatic time period of the infectious disease;

upon determining the statistically significant anomaly, generating an alert indicative of the non-symptomatic time period of the infectious disease; and providing the alert during the non-symptomatic time period to the UI, wherein the smart watch provides a non-invasive method for detecting an infectious disease.

10. A non-transitory computer-readable storage medium, the non-transitory computer-readable storage medium storing instructions to be implemented on a smart watch including at least one processor, the instructions when executed by the at least one processor cause the smart watch to perform a method for detecting an infectious disease within a person during a non-symptomatic time period of the infectious disease in a person in a non-clinical setting, the method comprising:

applying an age, a gender, and a body mass index (BMI) of the person to a multi-variate detection model, wherein the multi-variate detection model includes a principal component analysis (PCA) model and a buffer for storing past data;

collecting first cardiac data by sampling a photoplethysmography (PPG) sensor on the smart watch at a rate greater than 200 Hertz over a first time period and storing the first cardiac data in a buffer;

collecting first activity level data by sampling an accelerometer on the smart watch at a rate greater than 10 Hertz over the first time period and storing the first activity level data in the buffer;

applying the first cardiac data and the first activity level data to the multi-variate detection model;

applying a first time of day associated with the first time period to the multi-variate detection model;

applying first body position data of the person associated with the first time period to the multi-variate detection model;

collecting second cardiac data by sampling the PPG sensor at a rate greater than 200 Hertz over a second time period and storing the second cardiac data in the buffer;

collecting second activity level data by sampling the accelerometer at a rate greater than 10 Hertz over the second time period and storing the second activity level data in the buffer;

applying a second time of day associated with the second time period to the multi-variate detection model;

applying second body position data of the person associated with the second time period to the multi-variate detection model;

characterizing the first cardiac data and the first activity level data as baseline data including:

associating the first time period with a non-infected time period of the person; and determining an upper control limit based on the non-infected time period of the person;

continuously updating the buffer to remove long term trends via the PCA model;

determining in near real-time a statistically significant anomaly within the second cardiac data using the multi-variate detection model including the upper control limit, wherein the statistically significant anomaly is associated with the non-symptomatic time period of the infectious disease;

upon determining the statistically significant anomaly, generating an alert indicative of the non-symptomatic time period of the infectious disease; and providing the alert during the non-symptomatic time period to a user interface (UI) on the smart watch, wherein the method is a non-invasive method implemented by the smart watch.

11. A method implemented on a smart watch for detecting an infectious disease within a person during a non-symptomatic time period of the infectious disease in a non-clinical setting, the method comprising:

applying an age, a gender, and a body mass index (BMI) of the person to a multi-variate detection model, wherein the multi-variate detection model includes a principal component analysis (PCA) model and a buffer for storing past data;

collecting first cardiac data by sampling an electrocardiogram (ECG) sensor on the smart watch at a rate greater than 200 Hertz over a first time period and storing the first cardiac data in a buffer;

collecting first activity level data by sampling an accelerometer on the smart watch at a rate greater than 10 Hertz over the first time period and storing the first activity level data in the buffer;

applying the first cardiac data and the first activity level data to the multi-variate detection model;

applying a first time of day associated with the first time period to the multi-variate detection model;

applying first body position data of the person associated with the first time period to the multi-variate detection model;

collecting second cardiac data by sampling the ECG sensor at a rate greater than 200 Hertz over a second time period and storing the second cardiac data in the buffer;

collecting second activity level data by sampling the accelerometer at a rate greater than 10 Hertz over the second time period and storing the second activity level data in the buffer;

applying a second time of day associated with the second time period to the multi-variate detection model;

applying second body position data of the person associated with the second time period to the multi-variate detection model;

characterizing the first cardiac data and the first activity level data as baseline data including:

associating the first time period with a non-infected time period of the person; and determining an upper control limit based on the non-infected time period of the person;

continuously updating the buffer to remove long term trends via the PCA model;

determining in near real-time a statistically significant anomaly within the second cardiac data using the multi-variate detection model including the upper control limit, wherein the statistically significant anomaly is associated with the non-symptomatic time period of the infectious disease;

upon determining the statistically significant anomaly, generating an alert indicative of the non-symptomatic time period of the infectious disease; and providing the alert during the non-symptomatic time period to a user interface (UI) on the smart watch, wherein the method is a non-invasive method implemented by the smart watch.

12. A non-transitory computer-readable storage medium, the non-transitory computer-readable storage medium storing instructions to be implemented on a smart watch including at least one processor, the instructions when executed by the at least one processor cause the smart watch to perform a method for detecting an infectious disease within a person during a non-symptomatic time period of the infectious disease in a person in a non-clinical setting, the method comprising:

applying an age, a gender, and a body mass index (BMI) of the person to a multi-variate detection model, wherein the multi-variate detection model includes a principal component analysis (PCA) model and a buffer for storing past data;

collecting first cardiac data by sampling an electrocardiogram (ECG) sensor on the smart watch at a rate greater than 200 Hertz over a first time period and storing the first cardiac data in a buffer;

collecting first activity level data by sampling an accelerometer on the smart watch at a rate greater than 10 Hertz over the first time period and storing the first activity level data in the buffer;

applying the first cardiac data and the first activity level data to the multi-variate detection model;

applying a first time of day associated with the first time period to the multi-variate detection model;

applying first body position data of the person associated with the first time period to the multi-variate detection model;

collecting second cardiac data by sampling the ECG sensor at a rate greater than 200 Hertz over a second time period and storing the second cardiac data in the buffer;

collecting second activity level data by sampling the accelerometer at a rate greater than 10 Hertz over the second time period and storing the second activity level data in the buffer;

applying a second time of day associated with the second time period to the multi-variate detection model;

applying second body position data of the person associated with the second time period to the multi-variate detection model;

characterizing the first cardiac data and the first activity level data as baseline data including:

associating the first time period with a non-infected time period of the person; and determining an upper control limit based on the non-infected time period of the person;

continuously updating the buffer to remove long term trends via the PCA model;

determining in near real-time a statistically significant anomaly within the second cardiac data using the multi-variate detection model including the upper control limit, wherein the statistically significant anomaly is associated with the non-symptomatic time period of the infectious disease;

upon determining the statistically significant anomaly, generating an alert indicative of the non-symptomatic time period of the infectious disease; and providing the alert during the non-symptomatic time period to a user interface (UI) on the smart watch, wherein the method is a non-invasive method implemented by the smart watch.

* * * * *